(12) United States Patent
Garshong, Sr.

(10) Patent No.: US 12,029,876 B1
(45) Date of Patent: Jul. 9, 2024

(54) MEDICAL TUBING ORGANIZATIONAL DEVICE AND METHOD OF USE

(71) Applicant: Richard Kpakpo Garshong, Sr., Angier, NC (US)

(72) Inventor: Richard Kpakpo Garshong, Sr., Angier, NC (US)

( * ) Notice: Subject to any disclaimer, the term of this patent is extended or adjusted under 35 U.S.C. 154(b) by 0 days.

(21) Appl. No.: 18/438,021

(22) Filed: Feb. 9, 2024

(51) Int. Cl.
*A61M 39/10* (2006.01)

(52) U.S. Cl.
CPC ... *A61M 39/105* (2013.01); *A61M 2205/0216* (2013.01); *A61M 2205/0227* (2013.01)

(58) Field of Classification Search
CPC .............. A61M 39/105; A61M 25/02; A61M 2025/024; A61M 2205/584; A61M 2205/0216; A61M 2205/0227; F16L 3/223; F16L 3/2235
See application file for complete search history.

(56) References Cited

U.S. PATENT DOCUMENTS

| | | | | |
|---|---|---|---|---|
| 2,227,528 A * | 1/1941 | Adler | F16L 3/2235 174/157 |
| 3,421,187 A * | 1/1969 | Ryder | F16L 3/2235 D8/356 |
| D234,204 S * | 1/1975 | Miller et al. | D8/395 |
| 3,896,527 A * | 7/1975 | Miller | A61M 25/02 24/DIG. 22 |
| 4,775,121 A * | 10/1988 | Carty | F16L 3/2235 403/381 |
| 5,115,542 A * | 5/1992 | Gehres | F16L 3/2235 24/339 |
| 5,224,674 A * | 7/1993 | Simons | A61M 5/1418 604/80 |
| 5,389,082 A * | 2/1995 | Baugues | A61M 25/02 248/68.1 |
| 7,457,506 B1 * | 11/2008 | Osborne, II | F16L 3/2235 385/136 |
| 2001/0049504 A1 * | 12/2001 | Gautsche | A61B 46/23 604/179 |
| 2004/0118982 A1 * | 6/2004 | Shillings | F16L 3/223 248/68.1 |
| 2004/0135039 A1 * | 7/2004 | Reichert | F16L 3/223 248/68.1 |
| 2005/0006534 A1 * | 1/2005 | Shillings | F16L 3/223 248/68.1 |
| 2005/0077436 A1 * | 4/2005 | Nelson | F16L 3/223 248/68.1 |
| 2006/0237597 A1 * | 10/2006 | D'Andria | F16L 3/223 248/51 |
| 2014/0061421 A1 * | 3/2014 | Lane | F16L 3/221 248/542 |

* cited by examiner

*Primary Examiner* — Theodore J Stigell
(74) *Attorney, Agent, or Firm* — Ashley D. Johnson; Dogwood Patent and Trademark Law

(57) ABSTRACT

The invention is an organizing device that provides a structural frame adapted to receive and house a plurality of medical tubings (e.g., IV tubing). The device includes a central channel that extends from the rear face into an interior of the device. The device also includes a pair of side faces that include a plurality of tubing channels that extend from the first side face through the interior of the device to the second side face. Each tubing channel is in fluid communication and connects with the central channel. The device also includes a plurality of unique indicators, each corresponding to a particular tubing channel for ease of identification.

20 Claims, 10 Drawing Sheets

MEDICAL TUBING ORGANIZATIONAL DEVICE AND METHOD OF USE

TECHNICAL FIELD

The presently disclosed subject matter relates generally to an organizational device that can be used with a wide variety of medical tubing. As discussed in detail below, the disclosed device prevents tangling and the associated aggravation when medical tubing becomes intertwined during use. The device further allows each medical tubing to be quickly and easily identified by healthcare professionals.

BACKGROUND

A typical intravenous administration system includes a length of sterile flexible plastic intravenous tubing. One end of the tubing is attached to a supply reservoir, such as a bag that includes a prescribed medication or other liquid. The second end of the tubing is adapted to be inserted into a venous blood vessel of the patient via a needle or an infusion port coupled to a needle inserted appropriately into the patient. An infusion port provides a route of intravenous administration of one or more types of medications or other materials over a prolonged period of time through a common injection site. For example, intravenous (IV) drips provide the patient with continuous administration of saline and nutritional substances. Medications and other substances can also be administered intermittently through the same port or through the same IV drip.

It is common practice in a medical setting for patients to receive simultaneous, multiple intravenous medications or solutions through intravenous tubing. However, the simultaneous use of multiple intravenous fluid lines in an operating room, an intensive care room, and/or emergency room can result in confusion as to which IV connection routes to which particular insertion sites. Multiple intravenous tubes are long and transparent and frequently become entangled, intertwined, and/or twisted, making it even more difficult for the medical care provider to determine which medication is flowing through which intravenous tube. Safety, timely delivery of medication, and efficiency are paramount to critical care. In routine emergency situations or during surgical procedures, quick identification of a medicinal fluid source is often required.

To address the noted shortcomings, various methods of identifying and separating individual IV sets have been developed. For example, individual IV bags and tubing can be tagged or labeled at a single site by the attending physician or other personnel to identify an intended purpose. However, there is no standardization of such practices, which leads to confusion and wasted time spent looking up and down the IV set for identification. Other attempts include coloring the actual IV tubing. However, when medications are colored, problems can easily occur (e.g., a yellow IV set containing a medication that is blue could provide a misrepresentative or false appearance in the form of a green IV set). Other solutions include taping or clipping the various IV sets together into a bundle. However, the grouping of multiple IV sets with intermittent access ports can become confusing to users and is also very time consuming.

It would therefore be beneficial to provide an effective organizational system that can be used with IV tubing in a medical environment to overcome the shortcomings of the prior art.

SUMMARY

Figure 1A:
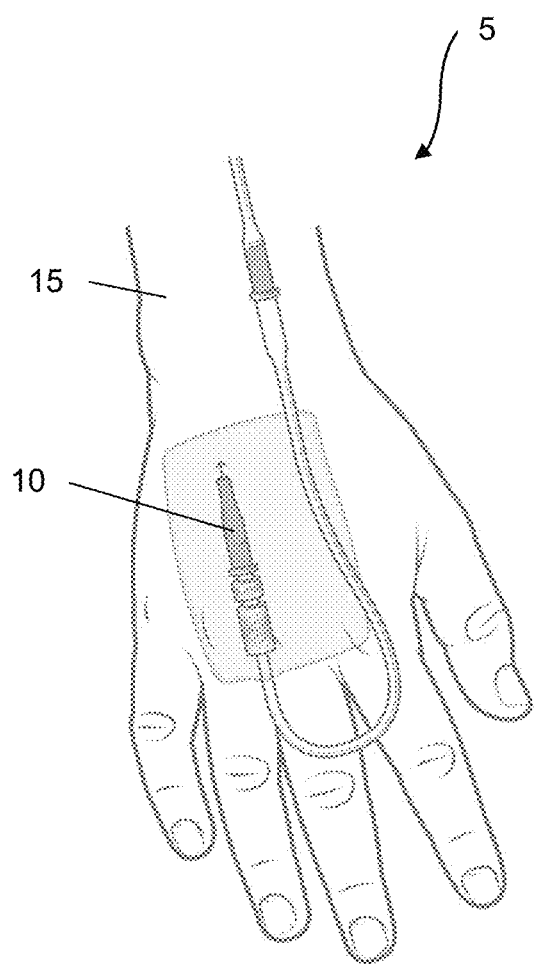
FIG. 1a is a top plan view of an injection port inserted into a patient hand in accordance with some embodiments of the presently disclosed subject matter.

The presently disclosed subject matter is directed to an organizational device comprising a top face and an opposed bottom face. The device also includes a front face and an opposed rear face comprising a central channel that extends into an interior of the device towards the closed front face. The device includes first and second opposed side faces, each side face including a plurality of tubing channels that extend from the first side face through the interior of the device to the second side face. Each tubing channel is in fluid communication and connects with the central channel. Each tubing is also positioned adjacent to the top or bottom face of the device. The device includes a plurality of indicators, each indicator corresponding to a designated tubing channel. Thus, each tubing channel comprises a first indicator positioned on the first and second side faces adjacent to the tubing channel and a second indicator positioned on either the top or bottom face of the device, adjacent to the tubing channel.

In some embodiments, the device includes a plurality of medical tubings, each tubing extending through a corresponding tubing channel, whereby the medical tubings are retained.

In some embodiments, the medical tubings include a diameter that is the same or about the same as a diameter of each of the tubing channels.

In some embodiments, the medical tubings are selected from IV line tubing, peripheral intravenous tubing, or combinations thereof.

In some embodiments, the central channel extends into a midline of the interior of the device.

In some embodiments, the organizational device includes 6-10 tubing channels configured in a double stacked orientation defined by an upper and lower tubing channel separated by the central channel.

In some embodiments, the organizational device includes an attachment element selected from a portion of adhesive, tape, double-sided tape, hook and loop closure, magnets, fasteners, or combinations thereof.

In some embodiments, each indicator includes a unique color when compared to the remaining indicators of the device.

In some embodiments, the organizational device is constructed from silicon, rubber, plastic, foam, or combinations thereof.

In some embodiments, the silicon, rubber, plastic, foam, or combinations thereof are transparent.

In some embodiments, the presently disclosed subject matter is directed to a kit comprising a plurality of the disclosed organizational devices and a plurality of medical tubings.

In some embodiments, the presently disclosed subject matter is directed to a method of preventing tangling of a length of tubings comprising a length, a first end, and a second end. Specifically, the method comprises positioning a first length of a first tubing through a tubing channel of the disclosed organizational device via the central channel. The method further includes positioning a first length of a second tubing through a tubing channel of the disclosed organizational device via the central channel. The method includes repeating the positioning step for each length of medical tubings. The first end of each tubing is then connected to an IV bag. The second end of each tubing is then connected to a patient via a needle or catheter. The lengths of the tubings are prevented from tangling together.

In some embodiments, the method further includes positioning a second length of each tubing through a tubing channel of a second organizational device.

In some embodiments, each length of tubing is releasably positioned in a corresponding tubing channel.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is directed to an organizational device that can be easily and effectively used with a wide variety of medical tubing. The term "organizational device" includes an element that can be used to sort and/or categorize elements such as medical tubings (e.g., so that they do not become intertwined and tangled). The term "medical tubing" refers to any type of tubing that can be used in association with inserting a fluid into a patient, including (but not limited to) catheters, guidewires, stents, shunts, IV lines, and the like. For example, suitable tubing can be conventional flexible tubing used in a variety of medical environments, such as to introduce or remove material into or from a patient (e.g., a wound site, vein, etc.). The term "tubings" or "tubing set" refers to a plurality of tubing. Thus, a tubing set can include a primary flow IV line, a second flow IV line, a third flow IV line, etc. A tubing set can also include a merging fluid pathway and various points to access the fluid pathway in some embodiments.

One specific example of medical tubing suitable for use with the disclosed device is peripheral intravenous (PIV) tubing. PIV tubing is a type of thin, flexible tubing that healthcare providers use to draw blood and administer treatments (e.g., IV fluids, medications, blood transfusions, delivery of total parenteral nutrition). After a provider inserts a PIV line in a patient, it can remain in place for several days, thereby preventing the need for repeated needle sticks. The most common location for insertion of a PIV line is the patient's upper extremities. One example of tubing 5 (e.g., PIV tubing) is illustrated in FIG. 1a. As shown, the tubing includes cannula 10 (a soft hollow tube that includes a needle attached at an end). The needle portion of the cannula is inserted into the vein of patient 15. Fluid communication is thereby established, allowing IV fluids and the like to be delivered to the patient from an IV bag or other source via the vein.

Figure 1B:
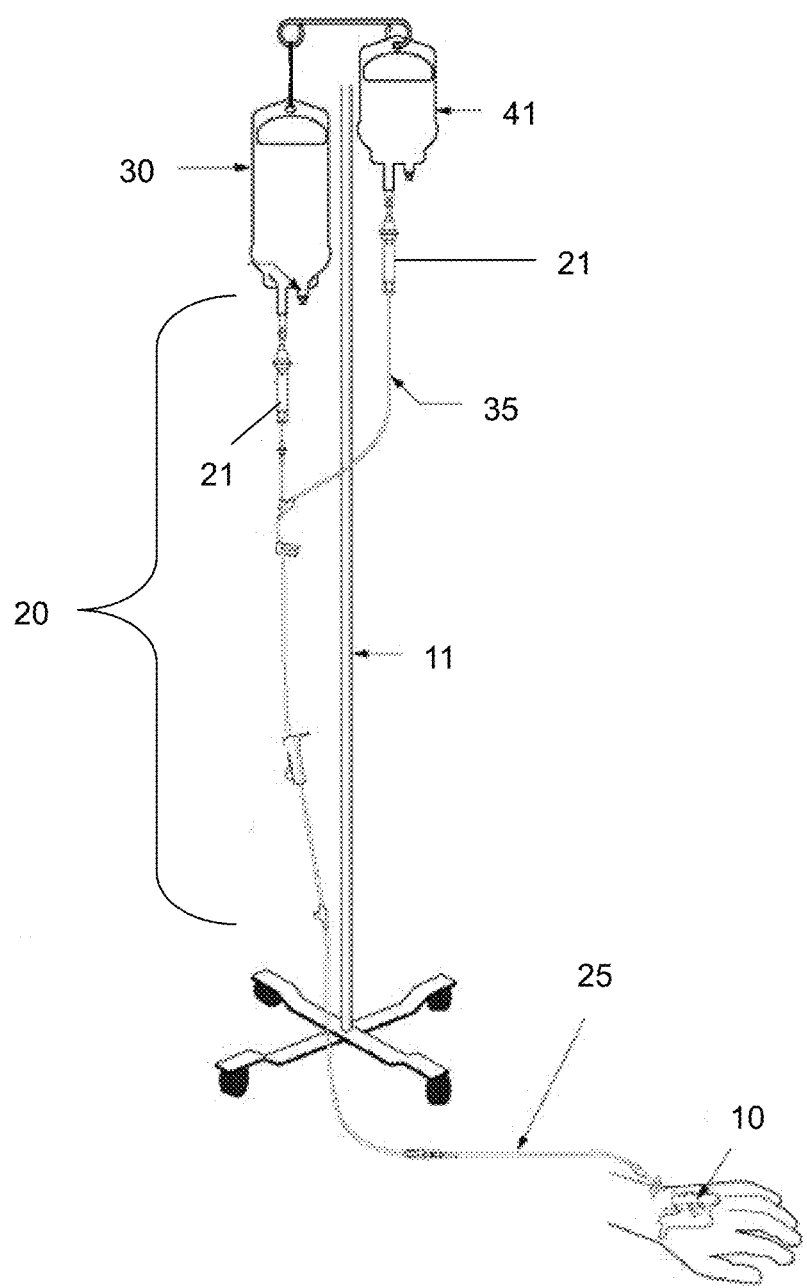
FIG. 1b is a front plan view of a standard IV pole with multiple IV bags in fluid connection with an injection port in a patient's hand in accordance with some embodiments of the presently disclosed subject matter.

The PIV tubing can be attached to a conventional IV pole 11 that holds several different tubing lines, as shown in the IV set of FIG. 1b. For example, cannula 10 can be attached to primary tubing 20 through one or more lengths of extension tubing 25. The tubing is connected to primary IV bag 30. The IV bag can be configured as a flexible plastic bag that serves as a container or reservoir for an IV drug solution (or any desired fluid). The set also includes drip chamber 21 having a hollow needle or spike adapted to puncture the bag. The drip chamber includes an outlet that communicates with a first segment of the primary tubing. In some embodiments, secondary tubing 35 can be used to allow for attachment of secondary IV bag 41. Often multiple different PIV tubes can be attached to a single patient 15. Due to the excess lengths of the tubing, it is not uncommon for the tubing to get tangled and intertwined, creating a hassle for medical professionals as well as a safety hazard. It should be appreciated that the disclosed device can be used with any of a wide variety of medical tubing and is not limited exclusively to PIV tubing.

Figure 2A:
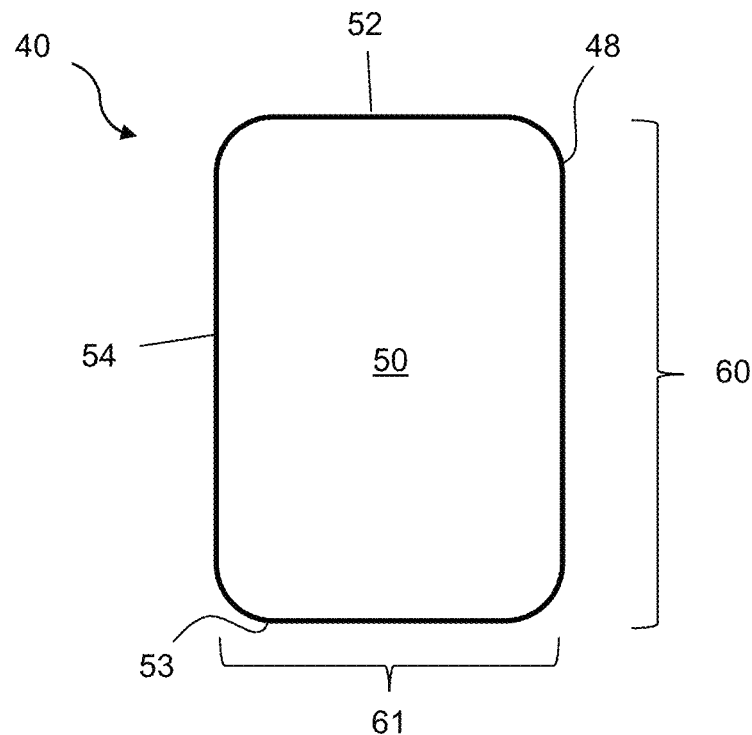
FIG. 2a is a top plan view of an organizational device in accordance with some embodiments of the presently disclosed subject matter.
Figure 2B:
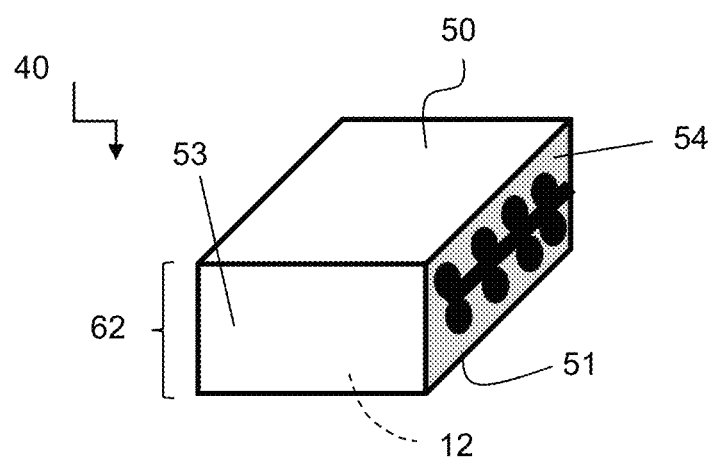
FIG. 2b is a perspective view of an organizational device in accordance with some embodiments of the presently disclosed subject matter.

To address the issue of tubing tangles and snags, the presently disclosed subject matter includes organizational device 40 that provides a structural frame adapted to receive and house a plurality of tubing 5. One embodiment of organizing device 40 is illustrated in FIGS. 2a-2b. As shown, the device includes opposed top and bottom faces 50, 51. In some embodiments, the bottom face of the device is configured to contact a support surface, such as the patient's skin distal to the IV insertion site, the floor, a medical cart, side table, and the like. Top face 50 is configured to oppose the bottom face, and face upwards, toward the ceiling in some embodiments. The device also includes open rear face 52 and opposed closed front face 53, as well as first (e.g., intake) side face 54 (from a pump) and second (e.g., exit) side face 48 (to patient), as shown in the top plan view of FIG. 2a. The open and closed front and rear faces allow for the insertion and retention of tubing 5 within the interior of the organizer, as discussed below. Thus, the "open" rear face refers to a face that includes a central channel (discussed below), while the "closed" front face lacks a central channel or any other type of opening.

Device 40 can have a square or rectangular cross-sectional shape as shown in FIG. 2b. However, the device is not limited and can be configured to have any desired cross-sectional shape, such as (but not limited to), circular, oval, triangular, pentagonal, hexagonal, octagonal, and the like. Any shape can be used.

Further, the disclosed device can include any desired dimensions. For example, in some embodiments, the device includes length 60 and/or width 61 of about 2-10 centimeters (e.g., at least/no more than about 2, 3, 4, 5, 6, 7, 8, 9, or 10 centimeters). The term "length" refers to the longest straight-line distance between front and rear 52, 53. The term "width" refers to the longest-straight line distance between first and second side faces 54 and 48.

The device can include thickness 62 of about 1-8 centimeters (e.g., at least/no more than about 1, 2, 3, 4, 5, 6, 7, or 8 centimeters). The term "thickness" refers to distance between top and bottom faces 50, 51.

It should be appreciated that the dimensions of device 40 are not limited, such that the length, width, and/or thickness can be greater or less than the ranges given above.

Figure 3A:
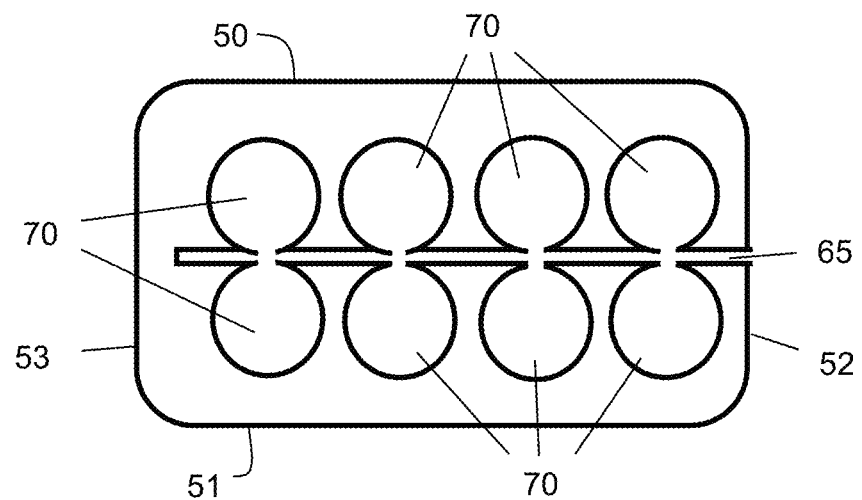
FIG. 3a is a side view of an organizational device in accordance with some embodiments of the presently disclosed subject matter.

Device 40 is configured to allow a plurality (e.g., 1, 2, 3, 4, 5, 6, 7, 8, 9, 10, or more) segments of tubing to pass therethrough to ensure that the various tubes do not become wrapped around each other, knotted, and the like. FIG. 3a illustrates one embodiment of side face 54 of the housing. As shown, the interior 12 of the housing includes central channel 65 that is in fluid communication with open side 52 only. The central channel thus passes from the rear face of the device, though the device interior along the first and second side edges 48, 54. The central channel does not extend all the way to front face 53 as shown in FIG. 3a. Although not limited to any particular configuration, the central channel can be positioned in the approximate midline of the device (e.g., about halfway between the top and bottom faces of the device). In such a configuration, each tubing can easily enter the interior of the device via the central channel and be maneuvered to a desired location.

Figure 3B:
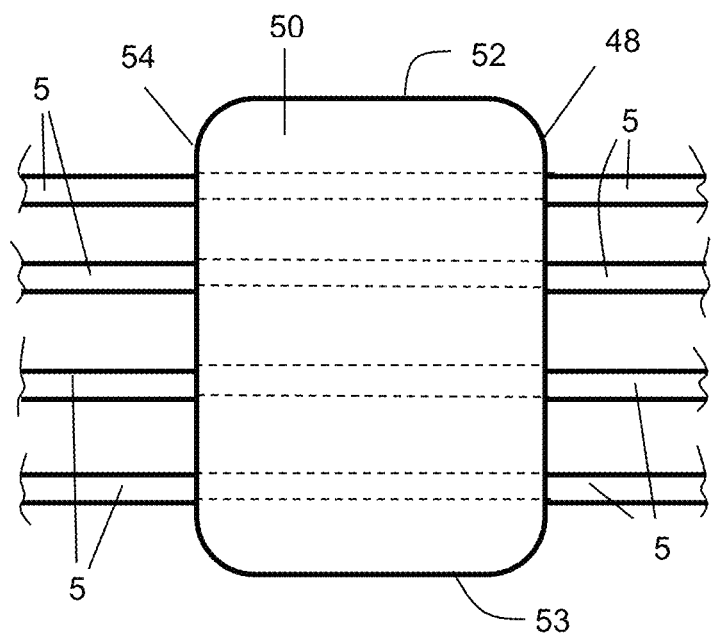
FIG. 3b is a top plan view of a system comprising an organizational device and a plurality of tubing in accordance with some embodiments of the presently disclosed subject matter.

The central channel is in fluid communication with each tubing channel 70, sized and shaped to house a particular tubing 5. "Fluid communication" refers to ability to move from one part, element, or component to another, or the state of being connected (e.g., an element can move through the central channel to each the tubing channels). As shown in FIG. 3b, each tubing channel spans the width of the housing within the housing interior, allowing individual tubes 5 to pass through. Stated another way, each tubing channel 70 is sized and shaped to allow a segment of tubing 5 to pass from first side 48, through the interior of the device, to exit via second side 54. In this way, each tube 5 is maintained in a spaced relationship relative to the other tubes and cannot become tangled. Once inserted into the tubing channel 70, each tube is securely retained until removed by medical personnel.

In some embodiments, the tubing channels can be arranged in a double stacked orientation (e.g., vertically or about vertically arranged as shown in FIG. 3a) with the central channel therebetween. However, the arrangement of the tubing channels is not limited and can include various modifications, such as an offset arrangement where each tubing channel is offset from adjacent tubing channels, a triple stacked arrangement where 3 tubing channels are vertically stacked, etc. Any arrangement can be used.

Figure 4A:
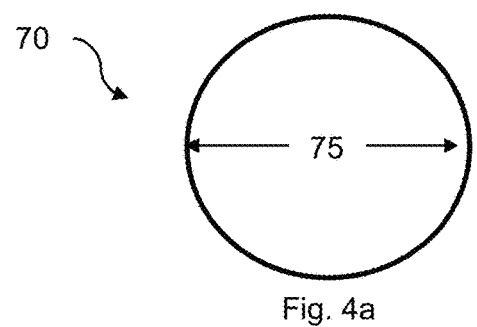
FIG. 4a is a cross-sectional view of an organizational device channel in accordance with some embodiments of the presently disclosed subject matter.
Figure 4B:
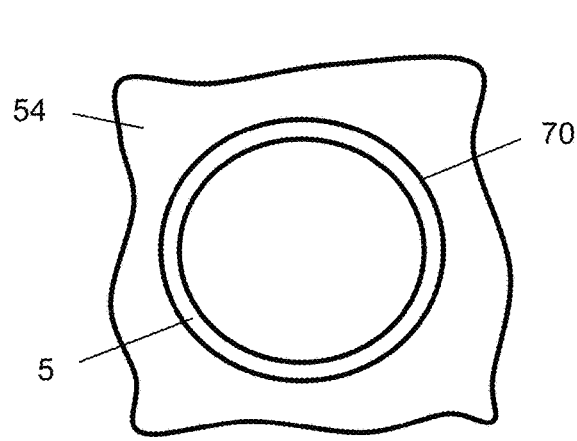
FIGS. 4b and 4c are cross-sectional views of organizational device channels comprising tubing in accordance with some embodiments of the presently disclosed subject matter.
Figure 4C:
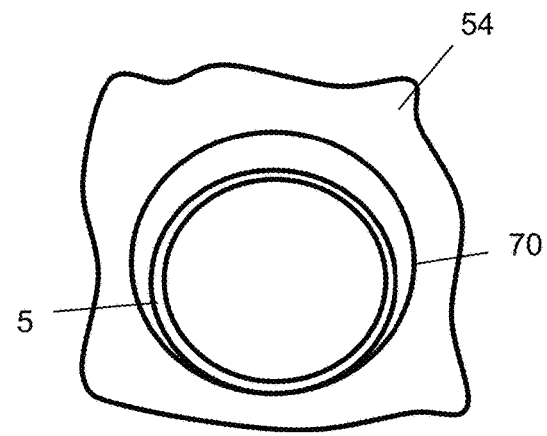

Each tubing channel can include diameter 75 of about 0.5 centimeters (e.g., at least/no more than about 0.25, 0.5, 1, 1.5, or 2 centimeters), as illustrated in FIG. 4*a*. The term "diameter" refers to the longest straight-line distance that passes through center of the cross-section of an element. In some embodiments, a corresponding tubing 5 can span about 100 percent of the diameter of the channel 70 (e.g., the tubing takes up the full interior of the channel), as shown in FIG. 4*b*. In other words, the outer surface of the tubing is in direct contact with the interior of the tubing channel. In other embodiments, tubing 5 takes up less than 100 percent of the volume of the channel (e.g., at least/no more than about 99, 95, 90, 85, 80, 75, 70, 65, 60, 55, or 50 percent), as illustrated in FIG. 4*c*. It should be appreciated that the appropriate diameter of tubing channel 70 will depend on the outside diameter of the medical line tubing and the intended fit of the tubing within the channel interior.

Figure 5:
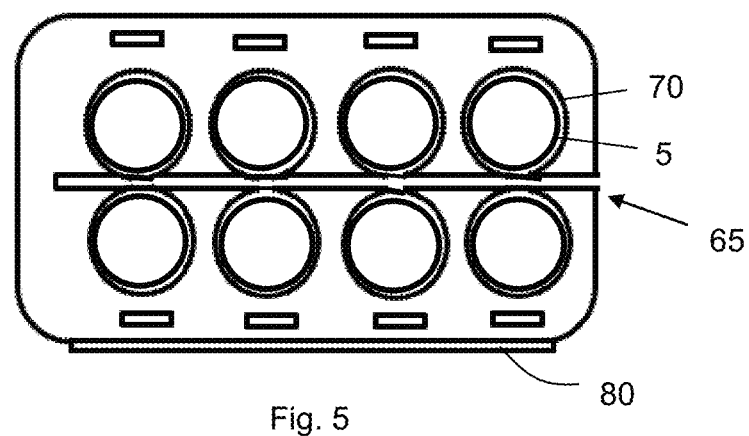
FIG. 5 is a side plan view of an organizational device in accordance with some embodiments of the presently disclosed subject matter.

Each tubing 5 is therefore removably coupled together with the device by passing through a designated tubing channel 70. Particularly, a segment of each tubing 5 enters the interior of the device via central channel 65 and is positioned to rest in a desired tubing channel 70. Because the tubing channel is open (or begins) at rear face 52, a tubing enters the central channel and can be easily maneuvered along the length of the central channel to a desired tubing channel. Once at a desired channel, the section of tubing can be positioned to rest solely within the designated channel, as shown in FIG. 5 (illustrating 8 tubing channels each with a corresponding section of tubing).

In some embodiments, the device can be releasably attached to a support surface (e.g., a wall, the floor, a table) using an attachment element 80. For example, in some embodiments, a portion of adhesive can be applied to a face of the device (e.g., top or bottom face), as shown in FIG. 5. It should be appreciated that the device is not limited to the use of adhesive, and any attachment element 80 can be used, such as (but not limited to) the use of magnets, VELCRO®, ties, staples, clips, single-sided tape, double sided tape, bolts, and the like. For example, an adhesive strip with a removable release liner can be used to allow the device to be affixed at a desired location.

Figure 6A:
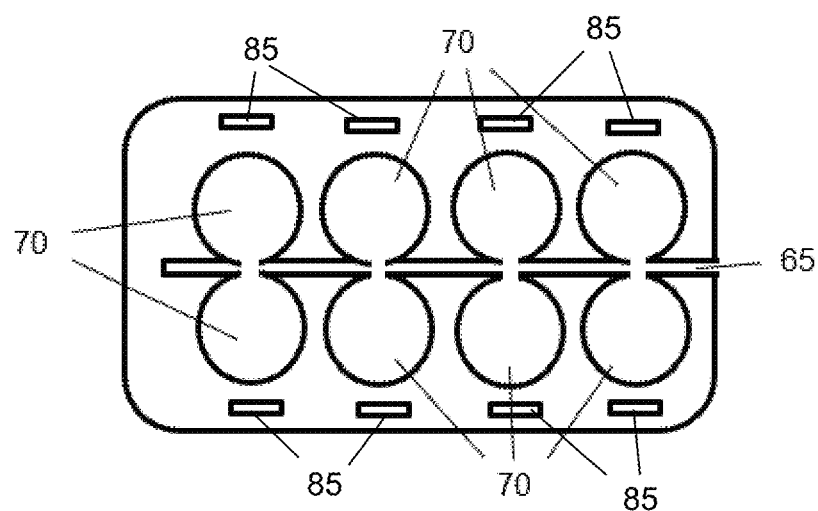
FIG. 6a is a side plan view of an organizational device in accordance with some embodiments of the presently disclosed subject matter.
Figure 6B:
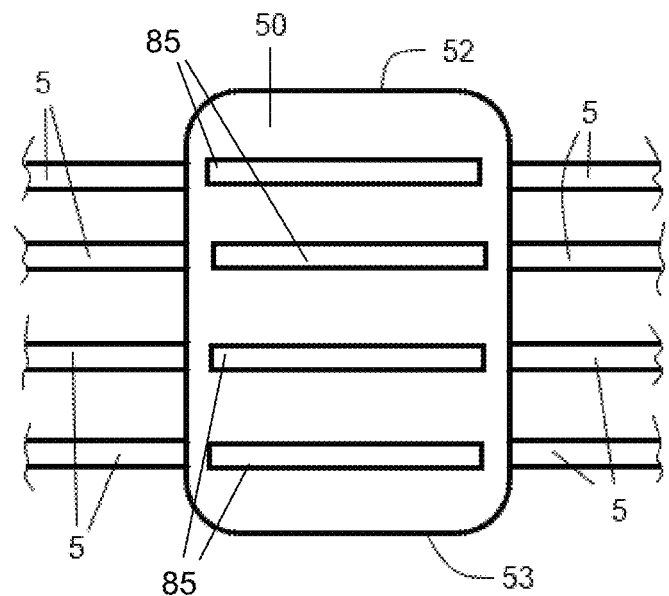
FIG. 6b is a top plan view of the organizational device of FIG. 6a in accordance with some embodiments of the presently disclosed subject matter.

In some embodiments, device 40 can include a plurality of indicators 85 positioned along the side, top, and/or bottom faces, adjacent to a corresponding tubing channel, as shown in FIGS. 6*a* and 6*b*. For example, side faces 48 and 54 can include a plurality of indicators, each positioned adjacent to an assigned tubing channel 70, as shown in FIG. 6*a*. Each indicator is unique relative to the other indicators 85 (e.g., a unique color). In this way, each tubing channel can be identified by the indicator. In some embodiments, both top and bottom faces 50, 51 of the device can also include corresponding indicators that run the width of the device, as shown in FIG. 6*b*. The term "indicator" broadly includes any visual that can be used to provide an identification.

Figure 7A:
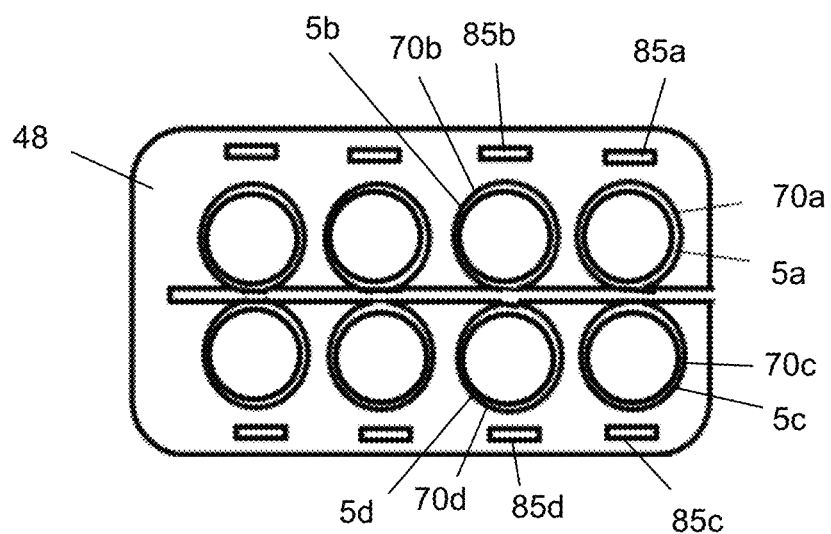
FIG. 7a is a first side view of an organizational device comprising a plurality of indicators in accordance with some embodiments of the presently disclosed subject matter.
Figure 7B:
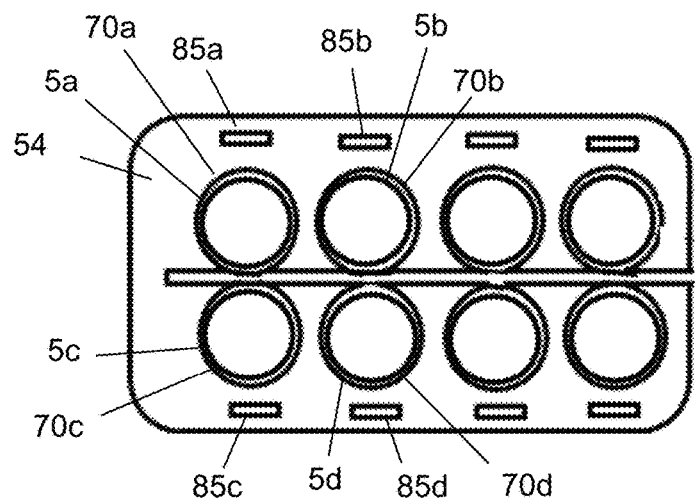
FIG. 7b is a second side view of an organizational device comprising a plurality of indicators in accordance with some embodiments of the presently disclosed subject matter.
Figures 7C, 7D:
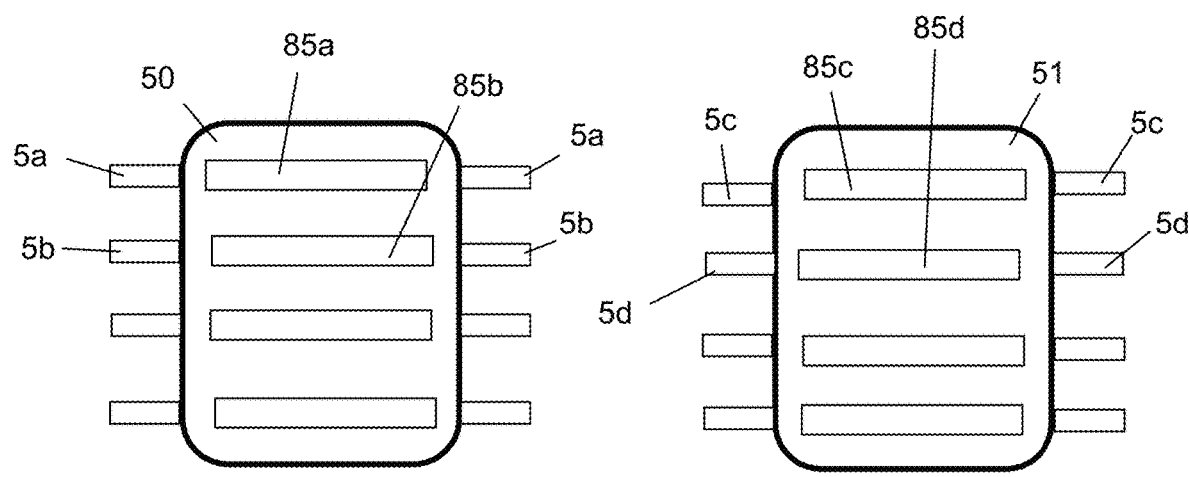
FIG. 7c is a top view of an organizational device comprising a plurality of indicators in accordance with some embodiments of the presently disclosed subject matter.
FIG. 7d is a bottom view of an organizational device comprising a plurality of indicators in accordance with some embodiments of the presently disclosed subject matter.

A first indicator (85*a*) is therefore present on first side face 54, second side face 48, and top face 50 to identify tubing 5*a* positioned in channel 70*a*. A second indicator (85*b*) is also present on first side face 54, second side face 48, and top face 50 to identify tubing channel 70*b* housing second tubing 5*b*, as illustrated in FIGS. 7*a*-7*c*. The first and second indicators would not be apparent on the bottom face of the device because the first and second tubing channels are positioned adjacent to the device top face. However, third and fourth indicators 85*c* and 85*d* positioned on the device bottom face identify tubing 5*c* and 5*d* housed in tubing channels 70*c* and 70*d*, respectively, as shown in FIG. 7*d*. The process is repeated for each tubing channel in the device (e.g., each of the side faces, top face, and bottom face can include an identifier to quickly differentiate one tubing channel/tubing from another).

Each indicator can be visually associated with a corresponding channel 70. For example, each indicator can be color-coded a unique color relative to the other indicators present on the device (e.g., a first indicator is blue, a second indicator is red, a third indicator is yellow, etc.). In this way, a health care practitioner can quickly and easily identify which particular tubing is located in which channel of the housing. In some embodiments, side faces 48 and 54 can include a plurality of indicators, each positioned adjacent to a tubing channel.

Thus, each indicator on device 40 can be assigned a unique color relative to the other indicators. Alternatively or in addition, each indicator can have a unique shape (e.g., triangle, square, circle, rectangle, star, etc.), a unique number (1, 2, 3, 4, etc.), a unique pattern (e.g., stripes, dots, checkerboard, etc.), a unique word, and the like relative to the other indicators of the device.

Device 40 can be constructed from any desired material, such as (but not limited to) silicon, rubber, plastic, foam, or combinations thereof. In some embodiments, the material or combination of materials selected for use with the device can be hypoallergenic such that contact with the skin of a patient or healthcare provider does not cause any adverse effects (e.g., irritation, rash). The term "hypoallergenic" refers to a material that causes fewer or no allergic reactions. Thus, when contact is made between a user's skin and a hypoallergenic material, no clinically discernible allergic reaction is produced.

In some embodiments, the device can be transparent, allowing visibility of each tubing 5 as it passes through the housing. As such, safety is increased as a user can track infusion of medications from an IV to the patient. The term "transparent" refers to a property of a material whereby the material permits transmission of at least 50% of the light directed to one side of the material through to the other side of the material. Thus, the housing can include a light transmission percentage of at least (or no more than) about 50, 55, 60, 65, 70, 75, 80, 85, 90, 95, or 99 percent.

In some embodiments, device 40 can be semi-transparent or can be opaque provided it has one or more apertures or windows through which a user may view the indicator. The term "semi-transparent" refers to an intermediate state between "transparent" and "opaque." The term "opaque" refers to materials that are either not transparent or are non-light transmitting over at least a portion of the visible light spectrum.

Figure 8:
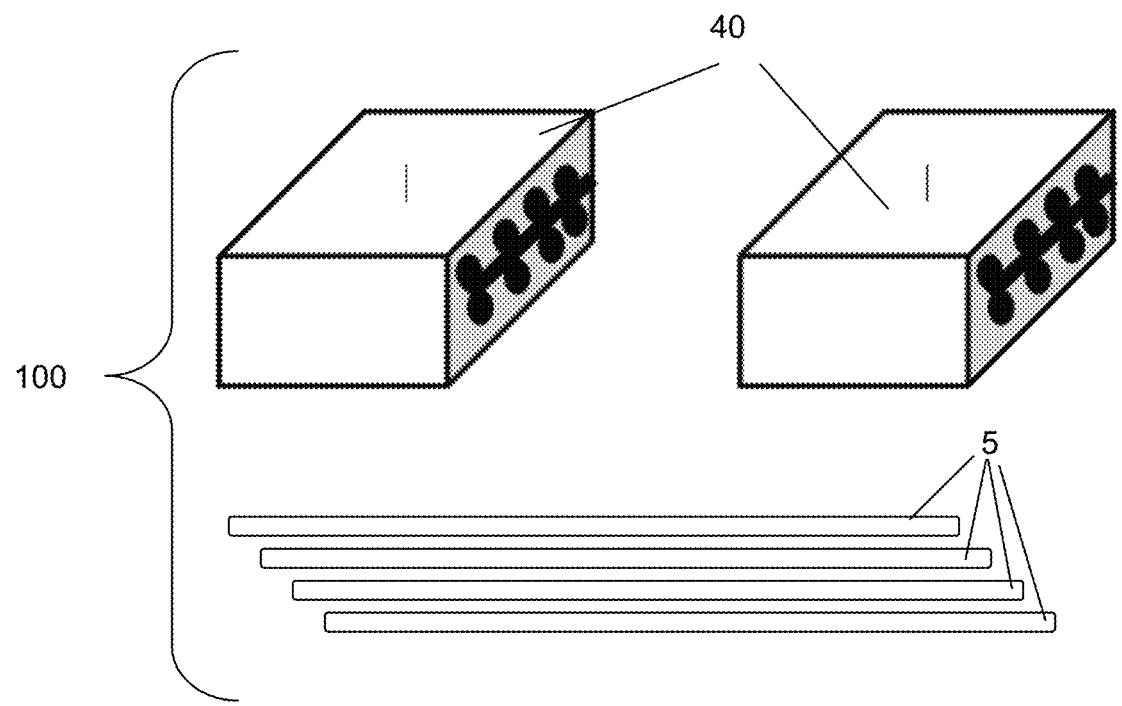
FIG. 8 is a perspective view of a kit comprising an organizational device in accordance with some embodiments of the presently disclosed subject matter.

In some embodiments, device 40 can be provided in the form of a kit for organizing and identifying a medical line. As shown in FIG. 8, kit 100 can include one or more devices 40 and a plurality of tubing 5. Each tube can be attached to a particular IV line (or other medical line) as would be known in the art. The kit can further comprise suitable packaging material and instructions for using the device to identify a medical line. In one embodiment, the packaging material provides a hermetic seal that indicates the sterility of the device contained therein.

Figure 9A:
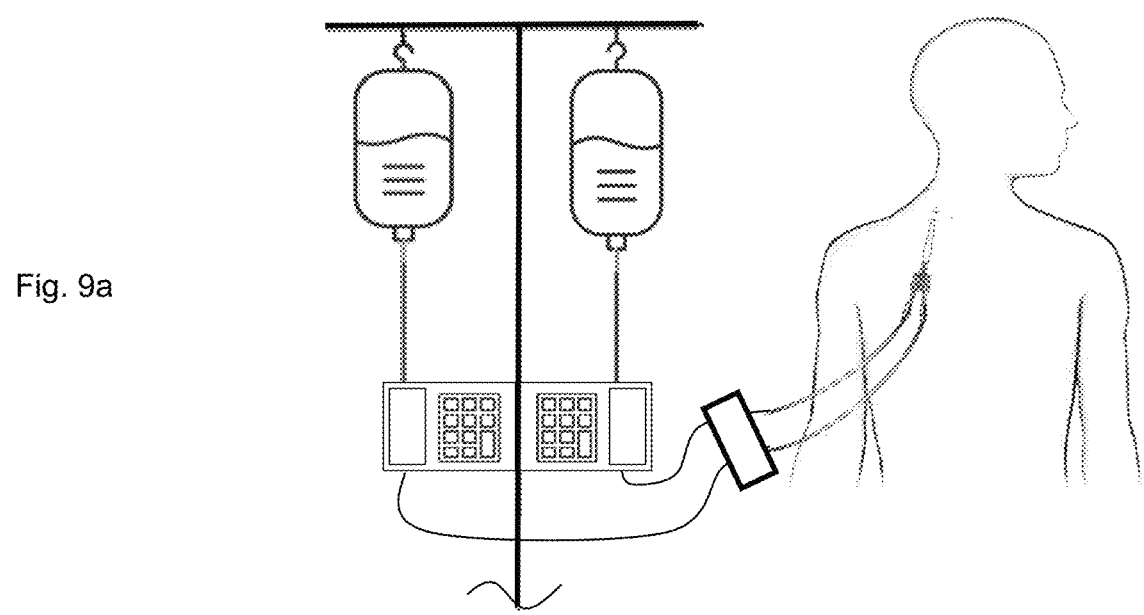
FIG. 9a is a schematic illustrating an organizational device in use in accordance with some embodiments of the presently disclosed subject matter.
Figure 9B:
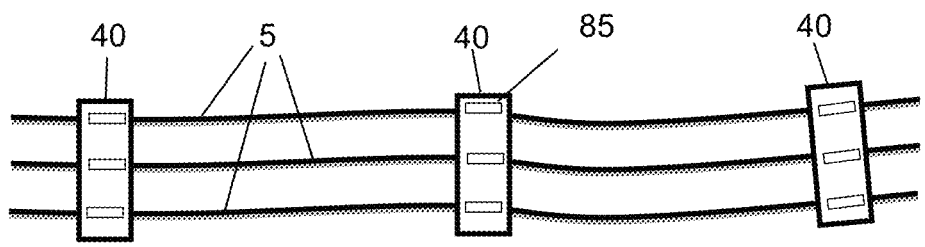
FIG. 9b is a fragmentary view of a plurality of organizational devices in use in accordance with some embodiments of the presently disclosed subject matter.

In use, the disclosed device can be used to effectively organize and coordinate a series of tubings 5. Each individual tubing is inserted into a corresponding channel 70 of the housing, passing through the housing interior via central channel 65. Thus, to insert a tubing into a desired tubing channel, the tube enters the interior of the device via the central channel on the rear device face. The tubing then travels along the length of the central channel until a desired tubing channel is reached, where the tubing then enters the tubing channel. Each tubing is associated with a unique identifier 85 (e.g., color coded) assigned with that particular channel (e.g., red is norepinephrine, blue is dopamine). In some embodiments, each tubing channel is configured to wrap around or contact a tubing such that friction maintains the tubing in place. The central channel allows for expansion to accommodate each tubing as it advances to a particular tubing channel. Once all of the tubing has been inserted into a corresponding channel and therefore assigned an indicator, the housing can be adhered to a support surface (e.g., the wall), as shown in FIG. 9*a*. In some embodiments, a plurality of housings can be positioned along a length of tubing to ensure that the tubings remain organized and do not tangle, as illustrated in FIG. 9*b*.

The device can be selectively utilized at sequential stages of medical care of the patient. By making a quick inspection of the patient's IV set system, subsequent attending personnel can quickly identify those procedures having been applied to the patient under prior medical procedures simply by examining the device and the various IV tubes therein to see which sets were used, how they were used, if they were used, etc. Further, the device ensures that the tubes remain organized and do not tangle. When the patient is discharged or the device is no longer needed, tubings 5 can be easily removed from channels 70 and the device reused on a new patient.

The disclosed device offers many improvements over current systems. For example, the disclosed device saves valuable time by preventing medical professionals from having to untangle medical tubing.

Device 40 also offers increased safety to patients. If dangerous tangles and knots in associated medical tubing are avoided, adverse effects are also minimized or eliminated.

Advantageously, the same device can be used across various stages of patient care associated with applications of multiple IV procedures.

Device 40 offers enhanced visual identification of the plurality of lines used during medical procedures.

The disclosed device minimizes confusion by medical professionals when confronted with a large mass of tangled IV tubing.

Device 40 retains medical tubing in a separated arrangement, making identification and maintenance of each tube easier.

The device indicators enhance the identification of the various IV tubing arrangements.

Device 5 can be rapidly assembled and taken apart without necessitating the utilization of any tools or with the help of conventional tools.

The device is also easy to use, requiring little to no training.

The device provides an initial cue to patient information, the details of which are provided on the patient chart.

Device 5 can also speed up the decision process by increasing the awareness of medical personnel with respect to the patient's treatment history.

Many modifications and other embodiments of the embodiments set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. An organizational device comprising:
 a top face and an opposed bottom face;
 a closed front face and an opposed rear face comprising a central channel that extends into an interior of the organizational device towards the closed front face;
 first and second opposed side faces, each side face including a plurality of tubing channels that extend from the first side face through the interior of the organizational device to the second side face, wherein each tubing channel is in fluid communication and connects with the central channel, and wherein each tubing channel is positioned adjacent to the top or bottom face of the organizational device;
 a plurality of indicators, each indicator corresponding to a designated tubing channel, wherein each tubing channel comprises a first indicator positioned on the first and second side faces adjacent to the tubing channel and a second indicator positioned on either the top or bottom face of the organizational device, adjacent to the tubing channel.

2. The organizational device of claim 1, further comprising a plurality of medical tubings, each tubing extending through a corresponding tubing channel, whereby the medical tubings are retained.

3. The organizational device of claim 2, wherein the medical tubings include a diameter that is the same or about the same as a diameter of each of the tubing channels.

4. The organizational device of claim 2, wherein the medical tubings are selected from IV line tubing, peripheral intravenous tubing, or combinations thereof.

5. The organizational device of claim 1, wherein the central channel extends into a midline of the interior of the organizational device.

6. The organizational device of claim 1, wherein the plurality of tubing channels comprises 6-10 tubing channels configured in a double stacked orientation defined by an upper and lower tubing channel separated by the central channel.

7. The organizational device of claim 1, further comprising an attachment element selected from a portion of adhesive, tape, double-sided tape, hook and loop closure, magnets, fasteners, or combinations thereof.

8. The organizational device of claim 1, wherein each indicator includes a unique color when compared to the remaining indicators of the organizational device.

9. The organizational device of claim 1, constructed from silicon, rubber, plastic, foam, or combinations thereof.

10. The organizational device of claim 1, wherein the silicon, rubber, plastic, foam, or combinations thereof are transparent.

11. A kit comprising a plurality of the organizational device of claim 1 and a plurality of medical tubings.

12. The kit of claim 11, wherein the medical tubings are selected from IV line tubing, peripheral intravenous tubing, or combinations thereof.

13. The kit of claim 11, wherein the medical tubings include a diameter that is the same or about the same as a diameter of each of the tubing channels.

14. The kit of claim 11, wherein the plurality of tubing channels comprises 6-10 tubing channels configured in a double stacked orientation defined by an upper and lower tubing channel separated by the central channel.

15. A method of preventing tangling of a length of tubings comprising a length, a first end, and a second end, the method comprising:
- positioning a first length of a first tubing through a tubing channel of the organizational device of claim 1 via the central channel;
- positioning a first length of a second tubing through a tubing channel of the organizational device of claim 1 via the central channel;
- repeating the positioning step for each length of medical tubings;
- connecting the first end of each tubing to an IV bag;
- connecting the second end of each tubing to a patient via a catheter or needle;
- wherein the lengths of the tubings are prevented from tangling together.

16. The method of claim 15, further comprising positioning a second length of each tubing through a tubing channel of a second organizational device of claim 1.

17. The method of claim 15, further comprising releasably attaching the organizational device to a support surface.

18. The method of claim 15, wherein the medical tubings are selected from IV line tubing, peripheral intravenous tubing, or combinations thereof.

19. The method of claim 15, wherein each length of tubing is releasably positioned in a corresponding tubing channel.

20. The method of claim 15, wherein each indicator includes a unique color when compared to the remaining indicators of the organizational device.

\* \* \* \* \*